United States Patent [19]

Corey

[11] 4,139,006
[45] Feb. 13, 1979

[54] FEMALE INCONTINENCE DEVICE

[76] Inventor: Arthur E. Corey, 5232 Oak Island Rd., Orlando, Fla. 32809

[21] Appl. No.: 778,952

[22] Filed: Mar. 18, 1977

[51] Int. Cl.$^2$ .............................................. A61F 5/46
[52] U.S. Cl. .................................. 128/127; 128/1 R; 128/DIG. 25
[58] Field of Search ............... 128/127, DIG. 25, 1 R, 128/341, 285

[56] References Cited

U.S. PATENT DOCUMENTS

| | | | |
|---|---|---|---|
| 2,638,093 | 5/1953 | Kulick | 128/DIG. 25 |
| 2,649,086 | 8/1953 | Sluijter | 128/DIG. 25 |
| 3,554,184 | 1/1971 | Habib | 128/DIG. 25 |
| 3,646,929 | 3/1972 | Bonnar | 128/1 R |
| 3,705,575 | 12/1972 | Edwards | 128/1 R |
| 4,019,498 | 4/1977 | Hawtrey et al. | 128/1 R |

*Primary Examiner*—Lawrence W. Trapp
*Attorney, Agent, or Firm*—Richard D. Dixon

[57] ABSTRACT

A device for controlling urinary incontinence in female patients. The device includes a body section for being inserted completely into the vagina. The body section includes a circumferential surface therearound for being gripped by the walls of the vagina for restricting the relative movement therebetween. A protruding section is rigidly attached to the body section and is oriented for displacing a surface of the superior wall of the vagina, and the urethra adjacent thereto, toward the pubic bone, thereby reducing the urethro-vesicle angle for further restricting the flow of urine through the urethra from the bladder to the urethral opening.

18 Claims, 5 Drawing Figures

FEMALE INCONTINENCE DEVICE

BACKGROUND OF THE INVENTION

1. Field of the Invention

This invention relates to medical devices used in controlling urinary incontinence in females. More specifically, this invention relates to devices which are completely inserted into the vagina for controlling the urethro-vesicle angle for regulating the flow of urine through the urethra from the bladder to the urethral opening.

2. Description of the Prior Art

Urinary incontinence in females has long been a serious problem for which no truly acceptable long term solution has been found. In severe cases of urinary incontinence, the female has no control of the excretion of urine from the bladder. This condition requires immediate medical attention and is often cured only by surgical means. However, in most circumstances the patient has some residual control over the urinating function, but cannot prevent the excretion of urine during stress situations such as coughing, sneezing, or physical exercise. At these times, the patient involuntarily releases a spurt of urine from the urethra when any type of pressure is exerted on the bladder. Even a small volume of urine which is allowed to contaminate the genital sections of the female can cause irritation and more importantly an offensive odor. The presence of the offensive odor can cause an antisocial attitude in the patient who fears that other people in the vicinity will take notice of the problem.

One solution to the problem of urinary incontinence is the use of absorbent pads in the genital section adjacent the urethral opening. These pads are genereally regarded as an unacceptable solution due to the limited volume of the urine which can be absorbed by the pads and the high probability of infection and inflammation of the skin exposed to the pad. Catheters may also be inserted into the urethra, but these catheters can cause infections and are generally only used during controlled circumstances, such as when the patient is under constant medical care in a hospital.

Surgical repair of the physical abnormality is also commonly practiced. In one type of operation a Kennedy stitch is used to secure the urethra to the periosteum of the pubic bone, which, if properly accomplished, results in a significant reduction in the urethro-vesicle angle. While this operation may be performed through an incision in the vaginal wall, it is also possible to accomplish the same repairs through an incision in the abdomen. While these surgical techniques are often effective for periods of several years, the urethra may break loose from its ties with the periosteum following extensive activity, thereby causing a recurrence of the urinary incontinence condition. The use of surgical techniques for relieving urinary incontinence is often not practical due to the age, health, or medical history of the patient. It should be noted that these surgical techniques are useful only in treating stress incontinence as opposed to neurogenic incontinence which results form a complete loss of control by the nervous system of the muscles controlling the urinary function.

Other inventors and medical specialists have discovered that by altering the angular relationship between the urethra and the bladder, the urinary incontinence can be regulated. By making the urethro-vesicle angle, which is defined between the urethra and the bladder, more acute, that is reducing the included angle between the urethra and the bladder, urinary incontinence can be significantly reduced.

In U.S. Pat. No. 3,705,575 Edwards discloses an incontinence device comprising of a first member which is adapted to fit within the vagina and which applies pressure to the urethra, and a second member adapted to bear against the external pubic area of the female body. The first and second members are coupled together by a generally U-shaped structure which resiliently urges the first and second members toward each other. As compared with the present invention, the Edwards device is uncomfortable to wear and can easily irritate the tender mucosal tissues adjacent the labia.

Habib in U.S. Pat. No. 3,554,184 discloses an incontinence device which is formed from silicone rubber and which is designed to be inserted into the anterior region of the vagina. A belt worn around the waist of the patient is coupled to the member and thrusts it upwardly against the superior wall of the vagina with a sufficient magnitude to effectively block the flow of urine through the urethra. The Habib device requires the wearing of an uncomfortable belt surrounding the waist of the patient. Also, the use of a device which is only partially contained within the vagina may cause serious irritation of the membranes of the labia.

Bonnar in U.S. Pat. No. 3,646,929 discloses a female incontinence device which comprises a generally flat support adapted for insertion into and retention by the vagina. A flexible diaphragm is coupled to the support and is inflated to expand in an upward direction against the superior wall of the vagina to exert pressure thereupon for applying pressure to block the urethra. As with the other inventions, the Bonnar device requires that a part of the apparatus must extend from the vagina, thereby increasing the probability of irritation to mucosal membranes surrounding the vagina. The inventions disclosed by Kulick in U.S. Pat. No 2,638,093 and Vincent in U.S. Pat. No. 3,080,865 are similar to the prior art patents already discussed.

Sluijter in U.S. Pat. No. 2,649,086 discloses a ring-shaped elastic member for being inserted into the vagina adjacent the opening thereof. The ring includes thereon an outwardly projecting thickened portion which is oriented to press against the superior surface of the vagina adjacent the opening thereof for closing off the "contractor" section of the urethra, that is the area adjacent the sphincter muscles adjacent the urethral opening. Whereas the Sluijter device exerts pressure to block the urethra opening — which means that the device must be removed from the vagina before the patient urinates — the present invention elevates a section of the urethra intermediate the bladder and the urethral opening for decreasing the urethro-vesicle angle — which means that the patient may urinate without removing the device from the vagina. Therefore, while the Sluijter device blocks all urine from flowing through the urethra, the present invention restores the natural geometry of the urethro-vesicle angle to allow the patient to naturally control the flow of urine.

SUMMARY OF THE INVENTION

The present invention relates to a device for being removably inserted into the vagina of a female patient for controlling urinary incontinence. In contrast to the prior art, the present invention comprises a body section for being inserted completely into the vagina, with the body section having a circumferential surface therearound for being gripped by the walls of the vagina for restricting the relative movement therebetween. A protruding section is rididly attached to the body section and is oriented for displacing a surface of the superior wall of the vagina, and an intermediate section of the urethra adjacent thereto, toward the pubic bone, thereby reducing the urethro-vesicle angle for restoring the patient's natural control of the flow of urine through the urethra from the bladder to the urethral opening.

In a first preferred embodiment of the present invention, the body section comprises a generally oval-shaped disc constructed of a pliable, resiliently deformable substance for being gripped by the walls of the vagina. The protruding section comprises paired distended appendages forming a continous section of the circumferential surface of the oval disc, with the paried distended appendages being juxtaposed on opposite sides of a major diameter of the oval disc for defining a generally U-shaped void therebetween. The U-shaped void acts to fold a section of the superior vaginal wall for slightly compressing an intermediate section of the urethra as it is displaced toward the pubic bone.

BRIEF DESCRIPTION OF THE DRAWINGS

Other objects, features, and advantages of the present invention will be clear from a study of the written description and the drawings, in which.

DETAILED DESCRIPTION OF THE PREFERRED EMBODIMENT

Figure 1:
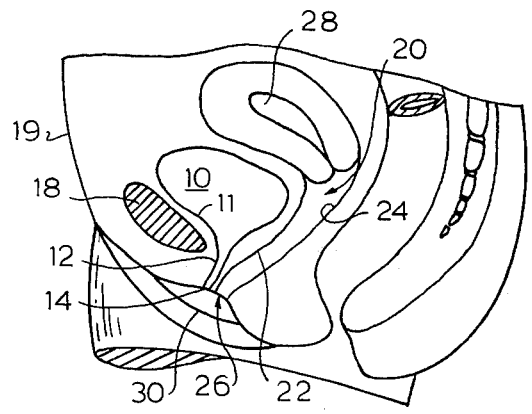
FIG. 1 illustrates a sagittal section of the female body showing the deformity of the urethro-vesicle angle, included between the urethra and the bladder, which can cause urinary incontinence.

The cross-sectional view of the lower portion of the female torso shown in FIG. 1 illustrates the location of organs in the female suffering from urinary incontinence. The bladder 10 stores the urine and passes it through the urethra 12 to the urethral opening 14 for discharge. The female patient, as illustrated in FIG. 1, has a very obtuse urethro-vesicle angle, which is the angle defined between the anterior surface 11 of the bladder 10 and the anterior surface of the urethra 12. The area of the urethro-vesicle angle is immediately adjacent to the posterior surface of the pubic bone 18. As previously discussed, surgical techniques for reducing the urethro-vesicle angle and therefore eliminating the incontinence problem involve the elevation and securing of the urethra 12 to the periosteum (not shown) surrounding the pubic bone 18. While the surgical techniques may provide temporary or medium term relief, it is not uncommon for the urethra 12 to break away from the periostium due to heavy physical activity or involuntary muscle action, such a coughing and sneezing, which produce large stresses upon the abdominal section of the patient.

One type of invention illustrated in the prior art utilizes a U-shaped resiliently deformable member, one end of which communicates with the pubic area 19 of the patient and the other end of which is inserted through the vaginal opening 26 for communicating with a superior surface 22 of the vagina shown generally as 20. Another type of invention illustrated in the prior art involves inserting a pneumatically expandable vessel into the vagina 20 for communicating with the inferior surface 24 thereof and expanding to produce a dislocation of the superior surface 22 of the anterior section of the vagina 20 adjacent the vaginal opening 26. Both of these inventions require a section of the invention to communicate out of the vaginal opening 26 which may cause irritation and infection in the area of the labia 30 which can spread through the vagina 20 into the uterus 28 causing serious complications.

Figure 2:
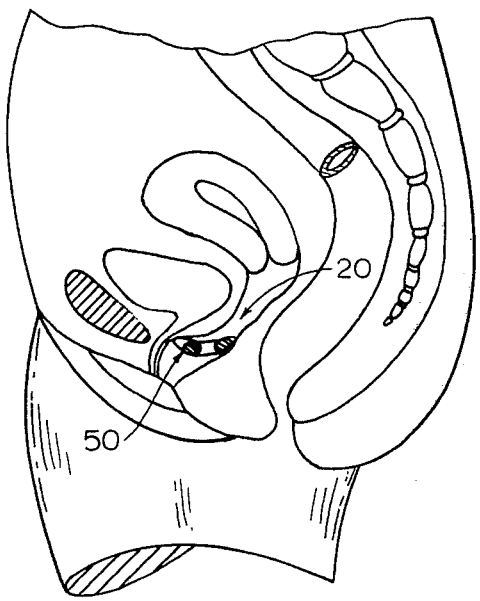
FIG. 2 illustrates a sagittal section of the female torso showing the insertion of the present invention into the vagina for reducing the urethro-vesicle angle.

In contrast to the prior art, the present invention, shown generally as 50 in FIG. 2, is inserted into and completely contained within the vagina 20 of the patient. In this manner, the opportunities for infection and irritation of the anterior vaginal mucossa and the labia are greatly reduced. A first preferred embodiment of the present invention is shown generally as 50 in FIGS. 3, 4, and 5. With specific reference to FIG. 4, the present invention is formed of a body section 60, having the form of a generally thin, oval-shaped disc or ring, and of a protruding section, shown generally as 80, which is rigidly attached to and formed as an integral part of the body section 60. As illustrated best in FIG. 3, the body section 60 is not a regular oval shape since a plurality of supplemental protrusions 61 are coupled to the circumference of the body section 60 which causes the overall shape of the body section 60 to be more irregular, thereby increasing the resistive coupling area of the vaginal walls which grip and hold the device 50.

A pair of supplemental protrusions 61 are spaced at opposite ends of a minor diameter of the body section 60, and a single supplementary protrusion 61 is located at the lower end of the major axis of the body section 60. A drainage aperture 62 is located generally at the intersection of the major and minor diameters of the body section, and allows vaginal drainage to migrate from the posterior end of the vagina 20 through the drainage aperture 62 toward the anterior end of the vagina and the vaginal opening 26.

The protruding section 80 is located generally at the opposite end of the major axis from the supplemental protrusion 61. While the protruding section 80 may have a variety of forms, its predominate purpose is to provice an additional displacement over and above which would be provided by the general oval or ring shape of the body section 60 for supplying additional pressure upon the superior wall 22 of the vagina 20 when the device 50 is inserted therewithin. In a first preferred embodiment, the protruding section 80 is formed from two, generally parallel distended appendages 81 and 82 which are oriented generally parallel to the major diameter of the body section 60 for increasing the effective length thereof. The distended appendages 81 and 82 define a generally U-shaped void 84 therebetween. This U-shaped void 84 is generally bisected by the major diameter of the body section 60 for providing a symmetrical force along this major diameter. The extension of the distended appendages 81 and 82, the separation therebetween, the depth and contour of the U-shaped void 84 together with the overall dimensions of the body section 60 are carefully determined to become comfortable and compatible with the anatomical structure of the female patient.

Figure 3:
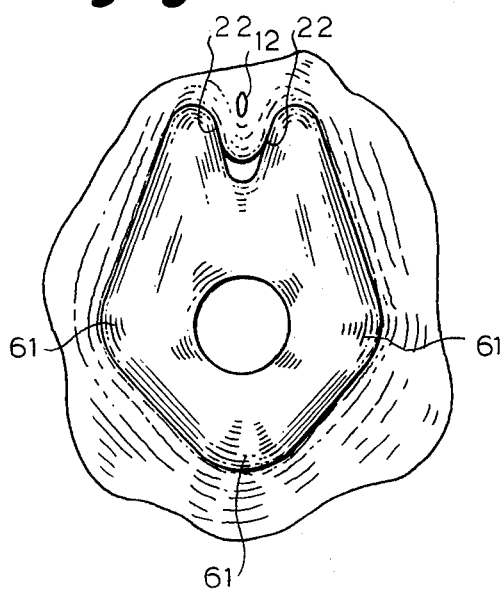
FIG. 3 illustrates a frontal view of the female vagina shown in FIG. 2 having the present invention inserted therein.

The length of the distended appendages 81 and 82 together with the depth and width of the U-shaped void 84 are specified for allowing a section of the superior vaginal wall 22 to fold therewithin as illustrated generally in FIG. 3. The device 50 is inserted within the anterior section of the vagina 20 so that the distended appendages 81 and 82 are on opposing sides of the urethra 12 in such a manner that the fold in the superior wall of the vagina 22 produces a lateral pressure upon an intermediate section of the urethra 12, thereby providing a slight reduction in the cross-sectional area of the urethra 12. This restriction of the cross-sectional area of the urethra 12 appears to have a second order effect of providing additional control against the spurting of urine through the urethra 12 responsive to unusual abdominal movements which produce pressure on the bladder 10. The distended appendages 81 and 82 provide additional irregularity to the overall shape of the device 50 which enhances the natural gripping ability of the vaginal walls for retaining the device 50 in its proper location during most types of physical activity.

Figure 5:
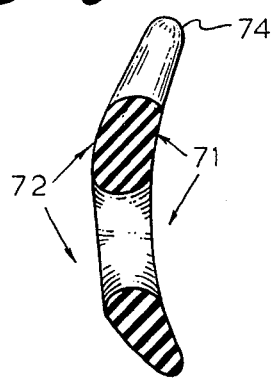
FIG. 5 illustrates a lateral cross-section view of the present taken along lines 5—5 as illustrated in FIG. 4.

The device 50 is molded as a smooth single unit composed of a pliable, resiliently deformable material, such as Dow Corning surgical elastomer MDX4-4514, which will readily deform as the device 50 is folded for insertion within the vagina 20 and during the normal physical activities of the female patient. In the first preferred embodiment, the present device 50 is molded from General Electric surgical grade silicon rubber. During clinical testing this substance has proven to be of sufficient elasticity to deform during physical activity while continually providing the required pressure upon the superior vaginal wall 22. As illustrated in FIG. 5, the unit comprising the body section 60 and the protruding section 80 is molded with a concave superior surface 71 which is designed to face upwardly within the vagina 20 generally adjacent to the superior surface 22 thereof.

The device also includes a convex inferior surface 72 which is designed to be adjacent with the inferior surface 24 of the vagina 20. The concave superior surface 71 and the convex inferior surface 72 intersect at a circumferential surface 74 about the perimeter of the device 50. The circumferential surface 74 is characterized by a relatively small radius of curvature around the periphery of the body section 60, with a somewhat increased curvature radius about the perimeter of the protruding section 80 to provide additional comfort to the patient in those areas in which the exerted pressure is the greatest. The convex inferior surface 72 is tapered sufficiently to provide a maximum of coupling area with the generally tubular shaped inferior surface 24 of the vagina 20 with which it couples.

Figure 4:
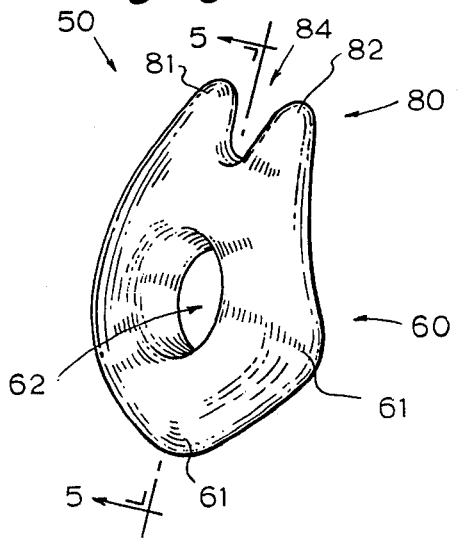
FIG. 4 illustrates a front perspective view of the first preferred embodiment of the present invention.

The operation of the present invention will now be illustrated with reference to FIGS. 2, 3, and 4. The device 50 for controlling incontinence in females may be inserted by the patient through the following procedures. First, the patient grasps the body section 60 of the device 50 at the supplemental protrusions 61 at opposing ends of the minor diameter of the body section 60. The patient then squeezes the body section 60 which generally will fold along the major diameter thereof. The device 50 is then inserted, large end first, into the vaginal opening 26 in a manner similar to a diaphragm for the prevention of conception. However, in contrast to the diaphragm which is inserted into the posterior end of the vagina adjacent the cervix of the uterus, the present device 50 is inserted only into the anterior end of the vagina adjacent the vaginal opening 26. The convex inferior surface 72 of the device 50 will be in sliding communication with the inferior surface 24 of the vagina 20 as the device 50 is inserted therewithin. As the convex inferior surface 72 of the device 50 slides along the inferior vaginal wall 24 due to pressure exerted upon the protruding section 80 and body section 60 of the device, the concave superior surface 71 of the device will deform to a reduced radius. As the device 50 approaches the proper location, the patient then locates the two distended appendages 81 and 82 comprising the protruding section 80 on opposing sides of the superior vaginal wall 22 so that the urethra 12 is generally centered above the U-shaped void 84. As pressure upon the protruding section 80 is released, the inferior and superior walls of the vagina will grip the circumferential surface 74 of the device 50, thereby securing the device in place. Due to the construction of the protruding section 80, the superior vaginal wall 22 and the urethra 12 adjacent thereto will be displaced in an anterior direction toward the pubic bone 18. The depth of insertion of the device 50 within the vagina 20 is controlled such that the protruding section 80 of the device 50 causes a displacement of a central section of the urethra 12 located between the bladder 10 and the urethral opening 14. This anterior or upward displacement of the urethra 12 is illustrated in FIG. 2 as causing a reduction in the urethro-vesicle angle defined between the anterior surface 11 of the bladder and the urethra 12. This dislocation of the urethra 12 causes the urethro-vesicle angle to become acute as the urethra 12 is moved closer to the pubic bone 18. Therefore, the present device 50 closely approximates the displacement of the urethra 12 which may be obtained by surgically connecting the urethra 12 to the periostium of the pubic bone 18. A small section of the superior vaginal wall 22 may fold within the U-shaped void 84 in the protruding section 80 as a result of the pressure exerted by the device 50. This folding of the vaginal wall 22 will produce a small pressure on the urethra 12 which may restrict the cross-sectional area of the urethra 12, thereby causing the second order effect of further restricting the flow of urine between the bladder 10 and the urethral opening 14.

After the device 50 is inserted within the vagina 20, the female patient may proceed with the normal physical activities characteristic of everyday life. The patient may even become active in physical activities such as tennis, volleyball, etc. which formerly would have been prohibited due to the danger of an unanticipated release of urine responsive to the increased abdomimal pressure caused by the the activities. The device 50 may be worn continuously within the vagina 20 of the patient without the necessity of frequent daily cleansings which are necessary with some other incontinence devices. Since the present device 50 supplements the natural uretral muscle action of the patient, it is not necessary to remove the device 50 when the patient desires to urinate. Instead, since the device 50 has displaced the urethra 12 to a position which corrects the deformity in the urethro-vesicle angle, the patient is now able to urinate satisfactorily even while the device 50 is in place within the vagina 20. If the device 50 has been fitted correctly by a qualified physician and has been inserted correctly by the patient into the proscribed area of the anterior section of the vagina 20, then the patient quickly will become acclimated to the presence of the device. In fact, after a very short period of time the female patient is able to undertake strenous physical activity without noticing the presence of the device 50.

While for the purposes of description I have shown and described a specific first embodiment of my invention, it will be apparent that changes and modifications can be made therein without departing from the spirit of my invention or the scope of the appended claims. For example, another preferred embodiment of the present invention would insert a wire reenforcing ring within the body section 60 and protuding section 80 for adding additional rigidity to the device. If recommended by the attending physician the size of the body section 60, that is the amount of material used to form the convex inferior surface 72 and the concave superior surface 71, may be greatly reduced thereby enlarging the drainage aperture 62. If prescribed by the attending physician, this reduction could result in the use of the wire ring having the same general shape as the present device 50 but covered with a similar plastic substance for effecting proper frictional cooperation between the device and the vaginal walls.

However, as is the case with the first preferred embodiment, the device must be designed to resiliently deform only in the original plane of the device for producing a generally uniform restoring force about the circumferential surface thereof.

Thus, a first preferred embodiment of the apparatus in accordance with the method of the present invention has been illustrated as an example of the invention as claimed. However, the present invention should not be limited in its application to the details illustrated in the accompanying drawings of the specification, since this invention may be practiced and constructed in a variety of different embodiments as previously discussed. Also, it must be understood that the terminology and descriptions employed herein are used solely for the purpose of describing the general operation of the preferred embodiment and therefore should not be construed as limitations on the operability of the invention.

I claim:

1. A device for being removably inserted into the vagina of a female patient for controlling urinary incontinence, said device comprising:

a body section for being inserted completely into the vagina, with said body section having a circumferential surface therearound for being gripped by the walls of the vagina for restricting the relative movement therebetween;

a protruding section rigidly attached to said body section and oriented for displacing a surface of the superior wall of the vagina, and an intermediate section of the urethra adjacent thereto, toward the pubic bone for reducing the urethro-vesicle angle, with said protruding section including means for folding a surface of the vaginal wall having the urethra adjacent thereto for laterally compressing the urethra therebetween, thereby restoring normal control of the flow of urine from the bladder to the urethral opening.

2. The device for controlling female incontinence as described in claim 1 wherein:

said body section comprises a generally oval shaped disc defining said circumferential surface therearound; and wherein said protruding section forms a continuous section of said circumferential surface and projects outwardly beyond said oval shaped disc for displacing a superior surface of the vaginal wall toward the pubic bone.

3. The device for controlling female incontinence as described in claim 2 wherein said oval shaped disc and said protruding section are oriented to provide a generally continuous concave superior surface which fits adjacent to superior wall of the vagina, whereby said protruding section will produce a larger anterior displacement of the superior vaginal wall toward the pubic bone.

4. The device for controlling female incontinence as described in claim 1 wherein said protruding section comprises paired distended appendages which define a generally U-shaped void therebetween, whereby a surface of the vaginal wall and the urethra juxtaposed therewith fold into said U-shaped void as said protruding section is displaced toward the pubic bone.

5. The device for controlling female incontinence as described in claim 2 wherein said circumferential surface about said oval shaped disc is beveled generally from a larger diameter at the surface adjacent the superior wall of the vagina to a smaller diameter adjacent to inferior wall of the vagina, whereby said bevel of said circumferential surface will more fully conform with the natural cross-sectional structure of the vagina.

6. The device for controlling female incontinence as described in claim 2 further including a plurality of supplemental protrusions attached to said body section and forming a continuous part of said circumferential surface for providing additional irregular shaped surfaces for being gripped by the walls of the vagina for restricting the relative motion therebetween.

7. The device for controlling female incontinence as described in claim 2 wherein said oval shaped disc includes an aperture therein for allowing vaginal drainage to migrate from the posterior section of the vagina to the anterior section thereof.

8. The device for controlling female incontinence as described in claim 1 wherein said body section and said protruding section are formed of a plyable, resiliently deformable material for conforming to the movements of the vagina during periods of physical activity of the female patient.

9. A device for controlling urinary incontinence in females, said device comprising:

a generally elliptical disc for being removably inserted completely within the vagina of the female, with said elliptical disc having a circumferential surface therearound for communicating with the vaginal walls for restricting the relative movement therebetween; and a pair of outwardly projecting appendages attached to said elliptical disc on opposing sides of a major diameter thereof for displacing a surface of the superior vaginal wall, and an intermediate section of the urethra adjacent thereto, toward the pubic bone, thereby correcting the urethro-vesicle angle for restoring natural patient control of the urinating function.

10. The device for controlling urinary incontinence in females as described in claim 9 wherein said paired projecting appendages extend outwardly from said elliptical disc in a direction generally parallel with a major diameter thereof, with said paired projecting appendages forming a generally U-shaped void therebetween for folding therein a section of the superior wall of the vagina having an intermediate section of the urethra adjacent thereto, thereby restricting the cross sectional area of the intermediate section of the urethra.

11. The device for controlling urinary incontinence in females as described in claim 10 wherein said paired projecting appendages and said elliptical disc are formed from a resiliently deformable material which deforms primarily within the plane of said elliptical disc.

12. The device for controlling urinary incontinence in females as described in claim 11 wherein a superior surface of said elliptical disc and said projecting appendages are generally concave in form.

13. The device for controlling female incontinence as described in claim 1 wherein said folding means partially reduces without fully closing the cross-section of the urethra, thereby allowing the normal and voluntary flow of urine through the urethra without removing said device from the vagina.

14. A device for being removably inserted into the vagina of a female patient for controlling urinary incontinence, said device comprising:
   a body section for being inserted completely into the vagina, with said body section having a circumferential surface therearound for being gripped by the walls of the vagina for restricting the relative movement therebetween; and
   protrusion means coupled to said body section for displacing by a selected distance toward the pubic bone a surface of the superior wall of the vagina and an intermediate section of the urethra adjacent thereto so as to reduce the urethro-vesicle angle without closing off the urethra, whereby the normal body muscles are then able to control the flow of urine from the bladder to the urethral opening without the necessity of removing said device from the vagina.

15. The device for controlling urinary incontinence as described in claim 14 wherein said body section comprises a resiliently deformable member generally foldable about a major axis thereof for facilitating the correct insertion of said device into the vagina of the patient.

16. The device for controlling female incontinence as described in claim 15 wherein said body section includes a plurality of arcuate outer circumferential surfaces, and further includes an aperature therein for allowing vaginal drainage to migrate from the posterior section to the anterior section of the vagina.

17. The device for controlling female incontinence as described in claim 14 wherein said protrusion means includes means for compressing the urethra, without closing off the urethra, between a folded surface of the vaginal wall, thereby further restricting without prohibiting the flow of urine from the bladder to the urethral opening.

18. The device for controlling female incontinence as described in claim 17 wherein said folding means comprises adjacent appendages which are coupled at an accute angle for defining a recess therebetween, whereby a surface of the vaginal wall and the urethra juxtaposed therewith fold into said recess as said protrusion means is displaced toward the pubic bone.

* * * * *